United States Patent
Bernard et al.

(10) Patent No.: US 9,861,323 B2
(45) Date of Patent: Jan. 9, 2018

(54) METHOD FOR OBTAINING TOMOSYNTHESIS IMAGES

(71) Applicant: General Electric Company, Schenectady, NY (US)

(72) Inventors: Sylvain Bernard, Montigny le Bretonneux (FR); Henri Souchay, Versailles (FR)

(73) Assignee: GENERAL ELECTRIC COMPANY, Schenectady, NY (US)

(*) Notice: Subject to any disclaimer, the term of this patent is extended or adjusted under 35 U.S.C. 154(b) by 525 days.

(21) Appl. No.: 14/065,864

(22) Filed: Oct. 29, 2013

(65) Prior Publication Data

US 2014/0119498 A1    May 1, 2014

(30) Foreign Application Priority Data

Oct. 30, 2012 (FR) .................................. 12 60364

(51) Int. Cl.
*A61B 6/02* (2006.01)
*A61B 6/00* (2006.01)

(52) U.S. Cl.
CPC .............. *A61B 6/025* (2013.01); *A61B 6/502* (2013.01); *A61B 6/5205* (2013.01)

(58) Field of Classification Search
CPC . G06T 2207/20012; G06T 2207/20028; A61B 6/025; A61B 6/502
See application file for complete search history.

(56) References Cited

U.S. PATENT DOCUMENTS

| | | |
|---|---|---|
| 2003/0076988 A1 | 4/2003 | Liang et al. |
| 2004/0105528 A1* | 6/2004 | Claus .................... G06T 11/005 378/210 |
| 2005/0123100 A1 | 6/2005 | Hsieh |
| 2007/0122021 A1* | 5/2007 | Zingaretti ............. G06T 7/0014 382/132 |

(Continued)

FOREIGN PATENT DOCUMENTS

| | | |
|---|---|---|
| FR | 2905256 A1 | 3/2008 |
| WO | 2009013970 A1 | 11/2009 |
| WO | 2009134970 A1 | 11/2009 |

OTHER PUBLICATIONS

Visser et al., Increase in perceived case suspiciousness due to local contrast optimization in digital screening mammography, Published on line Nov. 10, 2011, European Radiology, vol. 22, pp. 908-914.*

(Continued)

*Primary Examiner* — Glen Kao

(57) ABSTRACT

A method for obtaining tomosynthesis images of an object of interest using an imaging system, wherein the imaging system comprises an X-ray source arranged to facing a detector on which the object of interest is positioned. The method comprises acquiring a plurality of projected 2D images of the object of interest in a plurality of orientations identified relative to a perpendicular to the detector, wherein a zero orientation is closest to the perpendicular and applying at least one filter to the acquired projected 2D images to obtain filtered, projection images of the object of interest. The method further comprises determining a reconstruction slice of the object of interest from the backprojection of at least two of the filtered projections, the set of reconstruction slices being the filtered, reconstructed volume of the object of interest, wherein a filter used on the 2D projection images is an adaptive filter.

14 Claims, 3 Drawing Sheets

(56) References Cited

U.S. PATENT DOCUMENTS

| | | | |
|---|---|---|---|
| 2008/0056441 A1* | 3/2008 | Souchay et al. | 378/37 |
| 2008/0069294 A1* | 3/2008 | Wigstrom et al. | 378/4 |
| 2008/0130979 A1 | 6/2008 | Ren | |
| 2010/0226475 A1* | 9/2010 | Smith et al. | 378/37 |
| 2011/0150178 A1* | 6/2011 | Bernard | G06T 11/008 378/22 |
| 2011/0286651 A1* | 11/2011 | Yu et al. | 382/131 |
| 2012/0121064 A1* | 5/2012 | Bernard | 378/37 |

OTHER PUBLICATIONS

Sivaramakrishna et al., "Comparing the Performance of Mammographic Enhancement Algorithms: A Preference Study", 2000, American Journal of Roentgenology, vol. 175, pp. 45-51.*

Han et al., "A Novel Image Interpolation Method Using the Bilateral Filter", 2010, IEEE Transactions on Consumer Electronics, vol. 56, No. 1, pp. 175-181.*

21CFR1020.30 Code of Federal Regulation, Title 21, vol. 8, Section 1020.30, Revised Apr. 1, 2007, available at http://www.accessdata.fda.gov/scripts/cdrh/cfdocs/cfcfr/cfrsearch.cfm).*

Sone et al., Digital Image Processing to Remove Blur from Linear Tomography of the Lung, 1991, Acta Radiologica, vol. 32, pp. 421-425.*

French Search Report, dated Aug. 27, 2013

Claus et al., "Generalized Filtered Back-projection Reconstruction in Breast Tomosynthesis", International Workshop on Digital Mammography, pp. 167-174, 2006.

* cited by examiner

METHOD FOR OBTAINING TOMOSYNTHESIS IMAGES

BACKGROUND OF THE INVENTION

Embodiments of the present invention related to the general field of tomosynthesis.

A radiographic image is a projection of an object of interest. It is generally obtained by placing the object between an X-ray emitting source and an X-ray detector, so that the rays reach the detector after passing through the object. The radiographic image is then constructed from the data provided by the detector, and is an image of the object of interest projected onto the detector in the direction of the X-rays.

In this image, an experienced radiologist is able to distinguish radiological signs indicating a potential problem e.g. microcalcifications or opacities in mammography.

However, in a 2D projection image, the superimposition of tissues may hide lesions and under no circumstances can their actual position in the object of interest be known, since the radiologist has no information on the position of the radiological sign in the direction of projection.

Tomosynthesis has recently been developed to meet these problems; it allows a 3D image of an object of interest to be obtained in the form of a series of successive slices. These slices are reconstructed from projections of the object of interest from different angles. To do so, the object of interest is generally placed between an X-ray emitter source and an X-ray detector. The source and/or the detector are mobile so that the direction of the projection of the object onto the detector may vary (in mammography typically over an angle range of the order of 30° or more).

By looking at the tomosynthesis slices of an object of interest, a practitioner is therefore able not only to detect radiological signs in the object of interest but also to evaluate their 3D position.

Different techniques for reconstructing 3D images have been proposed allowing good quality reconstructed slices to be obtained with short computing times.

In particular, techniques using filtered backprojections (FBPs) have recently been proposed in patent US 2011/0150178 for example, or in the article:

"Generalized Filtered Backprojection Reconstruction in Breast Tomosynthesis"—Bernhard E. H. Claus, Jeffrey W. Eberhard, Andrea Schmitz, Paul Carson, Mitchell Goodsitt & Heang-Ping Chan, International Workshop on Digital Mammography, IWDM 2006, pp 167-174.

These techniques, in the projection images, particularly make use of high-pass filters which enhance the contrast of the structures. They provide image reconstruction of quality similar to that of the 3D images obtained with reconstruction techniques of iterative type, whilst allowing a limited number of iterations.

Three objects are illustrated in FIG. 1, one GS is of a large size and the two others, PS1 and PS2, correspond to structures of a smaller size, the object PS1 being more contrasted than the object PS2.

As illustrated in FIG. 1, it may happen with these techniques that contrast artefacts can be seen in the reconstructed images obtained, these propagating in the direction corresponding to the scanning of the X-ray beam when the source switches from one acquisition position to another. As can be seen by comparing the artefacts F of the beams generated in the image by the object PS1 and by the less contrasted object PS2, the more an object is contrasted the larger the artefacts and the more they are visible. In addition, the edge of the breast may at times appear to be highlighted which may be confused with an indirect sign of a lesion thereby inducing radiographer error.

Also, for interventional applications (biopsy, stereotactic surgery, etc.) highly contrasted metallic instruments may cause reconstruction artefacts that it is sought to reduce.

SUMMARY OF THE INVENTION

There is a need for an image reconstruction processing which has particularly short processing times and has further improved image quality.

Embodiments of the present invention provide a method for processing and displaying tomosynthesis images, and, more particularly, a method which allows both the display of reconstruction slices and the display of two-dimensional images (2D) of the object of interest.

Embodiments of the present invention can be applied in mammography.

According to an embodiment of the present invention, there is provided a method for obtaining tomosynthesis images of an object of interest by means of an imaging system. The imaging system comprises an X-ray source arranged facing a detector on which the object of interest is positioned. The method comprises the following steps: acquiring a plurality of 2D projection images of the object of interest in a plurality of orientations identified in relation to the perpendicular to the detector, one so-called zero orientation being the closest to the perpendicular; applying at least one filter to the acquired 2D projection images so as to obtain filtered, projection images of the object of interest; and determining reconstruction slices of the object of interest from the back projection of at least two of the filtered projections, the set of reconstruction slices being the filtered, reconstructed volume of the object of interest.

In an embodiment, a filter used on the 2D projection images is of an adaptive type.

In an embodiment, a filter applied to the projection images enhances the amplitude of the high frequencies of an image relative to the low frequencies of this image.

In an embodiment, a filter applied to the 2D projection images enhances the high frequencies with an amplification factor which varies according to the position of the pixel in the processed projection image.

In an embodiment, a filter applied to the 2D projection images enhances the high frequencies with an amplification factor which is a function of the local contrast of the processed projection image.

BRIEF DESCRIPTION OF THE FIGURES

Other characteristics objectives and advantages of the present invention will become apparent from the following description which is solely illustrative and non-limiting and is to be read with reference to the appended drawings, in which:

FIG. 3 schematically illustrates some operating functions of the imaging system according to an embodiment of the present invention;

DETAILED DESCRIPTION OF THE INVENTION

Figure 2:
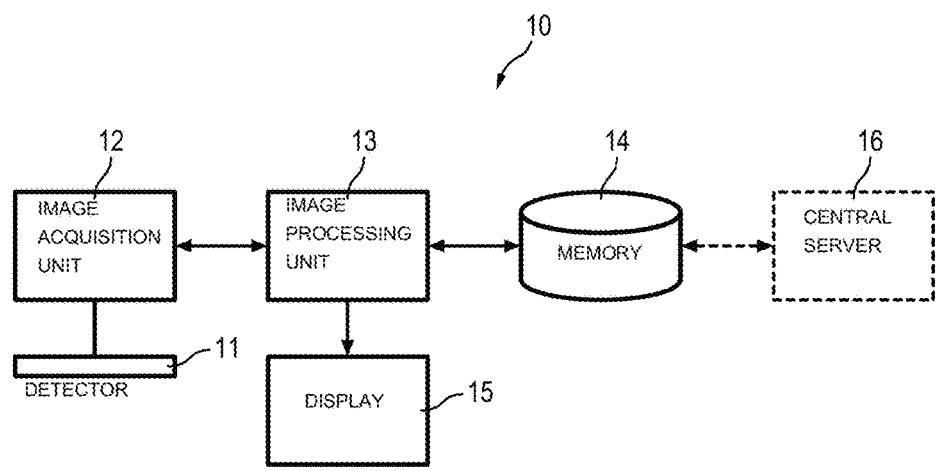
FIGS. 2 and 3 schematically illustrate an imaging system and its acquisition unit according to an embodiment of the present invention.

FIG. 2 schematically illustrates a medical imaging system 10 for acquiring projected 2D images to reconstruct a 3D image of a region of interest.

The medical imaging system 10 comprises an image acquisition unit 12, an image processing unit 13 and a display system 15.

Figure 3:
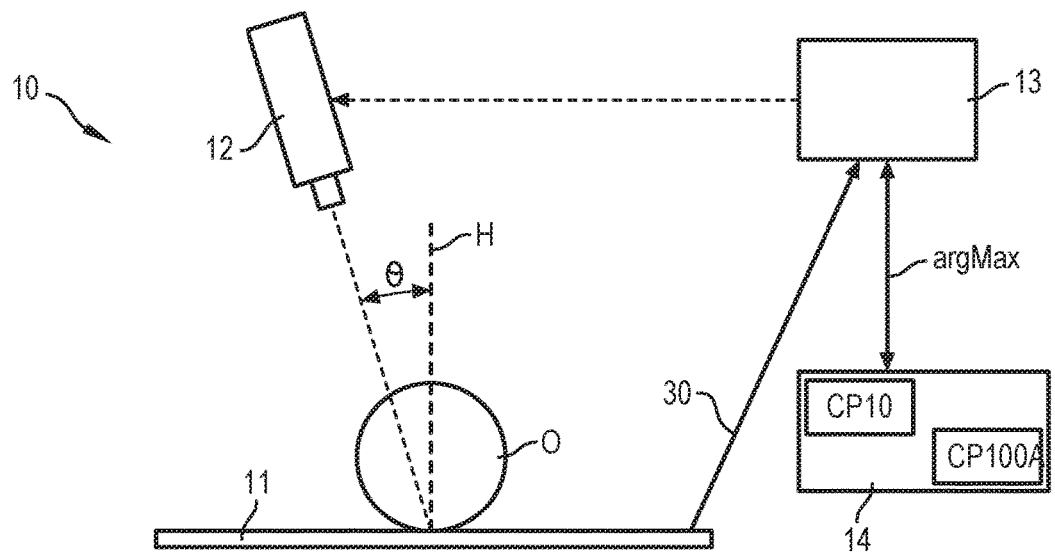

FIG. 3 schematically illustrates the acquisition unit 12.

The acquisition unit 12 allows a plurality of 2D projections to be obtained of a region of interest O—of an organ—in a patient. The acquisition unit 12 is notably formed by a detector 11 positioned facing an X-ray source 9. The detector 11 is a digital camera for example. The acquisition unit 12 is an X-ray acquisition system for example, the latter comprising any known means allowing the emitting of X-rays onto the object O and the acquisition of resulting images.

The display unit 15 can be integrated in the image acquisition unit 12 or the image processing unit 13, or it can be separate from the acquisition unit 12 and the processing unit 13. The display unit 15, for example, is a computer screen, a monitor, flat screen, plasma screen or any type of known commercially available display device. The display unit 15 enables a radiological practitioner to monitor the reconstruction and/or display of the acquired 2D images.

The processing unit 13 is adapted for implementing a processing method (e.g. the reconstruction of a 3D image from 2D images). The processing unit 13 can be integrated in the acquisition unit 12 or it can be separate from the acquisition unit 12. The processing unit 13, for example, is one or more computer(s), processor(s), microcontroller(s), micro-computer(s), programmable logic controller(s), application-specific integrated circuit(s), other programmable circuits or other devices which include a computer such as a work station.

The processing unit 13 is coupled to memory means 14 which may be integrated in or separate from the processing unit 13. These memory means may be formed by a hard disk or any other removable storage means (CD-ROM, floppy disc, etc.). These memory means may be used to store a 3D image of the region of the organ visualized as an acquired or processed 2D image. This may be a ROM/RAM memory of the processing unit 13, a CD-ROM, USB key, a memory of a central server 16. The processing unit 13 may comprise a read device (not illustrated) e.g. a floppy disc reader or CD-ROM reader, to read the instructions of the processing method (described in the remainder hereof) from an instruction medium (not illustrated) such as a floppy disc or CD-ROM. In an embodiment, the processing unit 13 executes the instructions of the processing method (described in the remainder hereof) that are stored in firmware (not illustrated).

Figure 4:
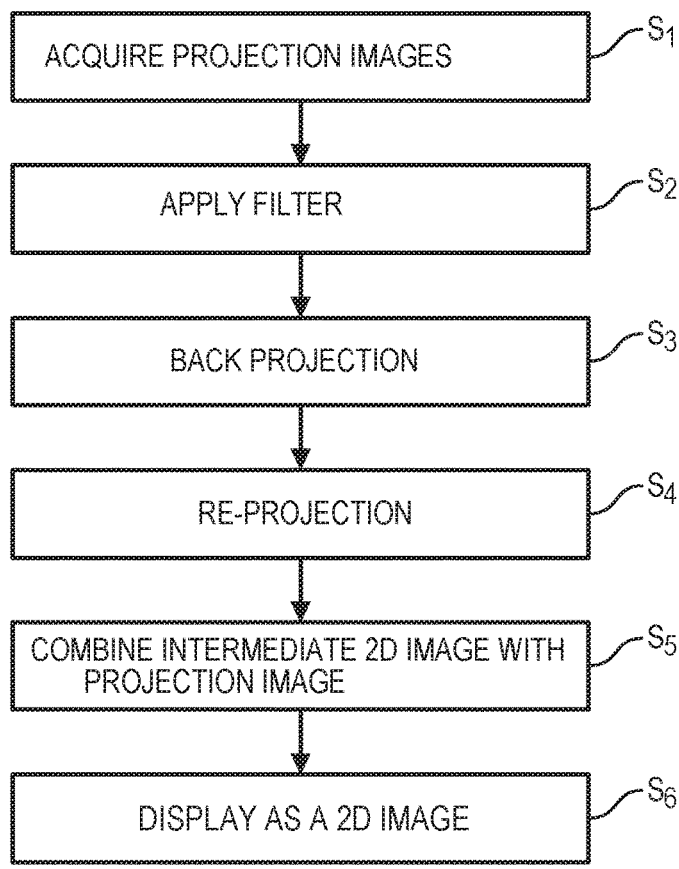
FIG. 4 is a block diagram showing the different steps of processing conforming to an embodiment of the present invention.

Acquisition and filtering of the projection images:

FIG. 4 illustrates different steps to obtain tomosynthesis images.

At a first step S1, a plurality of projected 2D images 30 are acquired of the object of interest O in a plurality of orientations around the object (scanning between −12° and +12° for example, or between −25° and +25°).

The method further comprises a step S2 to apply a filter to the acquired, projected 2D images 30 so as to obtain filtered, projection images 40 of the object of interest O.

To increase the quality of the reconstructed images, the filtering used on the projected pixels is adaptive filtering.

Different types of adaptive filters can be envisaged, in relation to the types of desired improvements.

Figure 1:
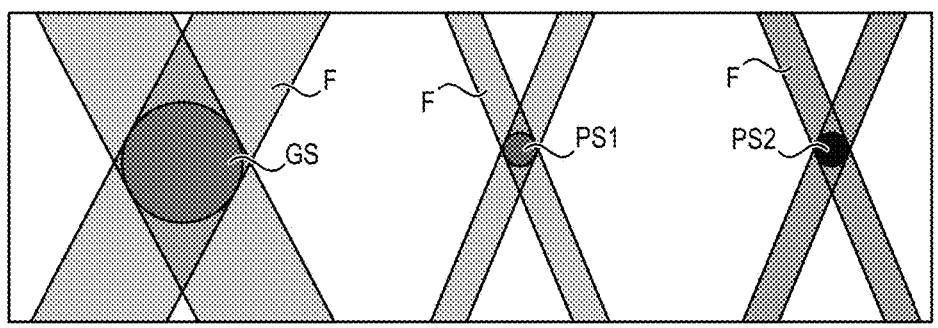
FIG. 1 illustrates the impact of small contrasted structures in an object to be imaged.

In particular, to reduce blurring which may be generated in projection images by structures of large size (reference can be made to FIG. 1 in which the object GS of large size generates a large fan-shaped artefact via its back projection), the adaptive filter can be chosen so as to enhance the amplitude of the high frequencies relative to the low frequencies.

For this purpose, the filtering used may be filtering of "Unsharp masking" type, each pixel p of (x, y) coordinates in the plane of projection being filtered in the following manner:

$$p'(x,y)=LP_\sigma(x,y)+\alpha\cdot[p(x,y)-LP_\sigma(x,y)],$$

where p'(x,y) is the value of this filtered pixel, a being an amplification factor, LP, being a low-pass filter applied to the value of the pixels around the pixel of (x,y) coordinates in the direction corresponding to scanning by the X-ray beams when the source switches from one acquisition position to another, and for example being:

$$LP_\sigma(x, y) = \int_{-Win}^{Win} p(x, y + v) \cdot G_\sigma(v) \cdot dv$$

where $G_\sigma$ is a Gaussian of standard deviation σ, Win is a parameter defining the size of the neighbourhood it is desired to take into account for the filter around the pixel of (x,y) coordinates.

With said filter, it is therefore possible to enhance the high frequencies relative to the low frequencies.

In an embodiment, this low-pass filter can be replaced by a bilateral filter, so as to avoid the effects of under-exposure which may otherwise exist on the edges of highly contrasted structures.

In addition, the amplification factor may itself be a function of the x, y coordinates of the points in the projection images. It can therefore be adapted to the local contrast of the objects/structures appearing in the processed projection image, in order to attenuate the impact of highly contrasted objects/structures in the reconstructed volume.

The local contrast in a projected pixel may be given by the difference between the value of the pixel and the value filtered by a low-pass filter for this pixel; in an embodiment, it can be given by the difference between the value of the pixel and the value filtered by a bilateral filter for this pixel.

In mammography, images may contain some contrast artefacts on the edges of the breast where the skin is thinner. The use of an amplification factor itself varying spatially, allows these effects to be corrected or attenuated.

For example, in the case of an adaptive low-pass filter, this can be expressed as:

$$p'(x,y)=LP_\sigma(x, y)+\alpha(x,y) \cdot [p(x, y)-LP_\sigma(x, y)],$$

with $$\alpha(x, y)=f(p(x, y)-LP_\sigma(x, y)),$$

where f is a function dependent on the local contrast and chosen to optimize the image quality of the reconstructed slices, and where f may depend on local contrast and depend on the distance from the pixel (x,y) to the edge of the breast.

In addition, the frequency on and after which the amplification is applied may depend on the thickness of the breast, the emission angle of the tube or the target angle thereof It will effectively be appreciated that these different parameters also have an effect on reconstruction artefacts. For example, the thicker the breast the greater the impact obtained by backprojection of a structure therein over the entire volume. Lower cut-off frequencies for example are therefore used for large breast thicknesses as well as higher coefficients of amplification.

The same applies to the angle of emission or target angle of the X-ray tube. For example, the larger these angles are, the greater the increase in the cut-off frequency of the filter used or in the amplification factor.

Reconstruction of the slices of the 3D image:

At a step S3, reconstruction slices 50 are determined of the object of interest O. This determination S3 particularly consists of a backprojection of the filtered, projected 2D images 40.

This backprojection may in particular be non-linear of the type "Order Statistics Based Backprojection". In linear backprojection, each voxel of the volume is reconstructed using N data pixels, each pixel being determined by reprojection of the voxel in each of the N projections. In non-linear backprojection, the pixel of maximum intensity among the Ns is not used, which makes it possible to obtain a distinct reduction in replication artefacts caused by the most intense objects.

It is noted that the reconstruction slices of the object of interest O represent the reconstructed volume of the object of interest O.

Optionally, at a step S4, the reconstruction slices 50 are re-projected in a given determined direction.

Examples of such reprojection processing have been described for example in patent application US 2011/0150178.

This makes it possible to obtain an intermediate 2D image 60 of the object of interest O.

At a step S5, this then gives a final 2D image of the object of interest by combining the intermediate 2D image 60 with a projection image initially acquired in a given orientation of the source (e.g. the orientation in which the said source emits perpendicular to the plane of the detector). The combination is, in an embodiment, pixel by pixel linear combination.

The final 2D image thus obtained is then an image similar to a mammography image and can be displayed (step S6).

In this manner, with one single reconstruction, it is possible to obtain both reconstructed slice images and a 2D image resembling a 2D radiography image of the object of interest.

As will be appreciated however; steps S4, S5 and S6 are optional.

It will be noted that the sampling of the images of reconstructed slices can be identical to that of a projection image, the backprojection and reprojection being performed in a single computing step, making it possible substantially to reduce the computing time.

In an embodiment, the reconstruction of an image of a sectional plane can be made in relation to the ratio between the zoom applied during backprojection and the zoom required for reprojection at one or more given incidences.

In this manner, a better definition is potentially obtained of some small objects, in particular of microcalcifications for example.

The different steps just described and in particular the processing steps S2 and S3 (and optionally S4 and S5) are implemented using code instructions of a programme recorded on a medium integrated in the processing unit or associated therewith.

Figure 5A:
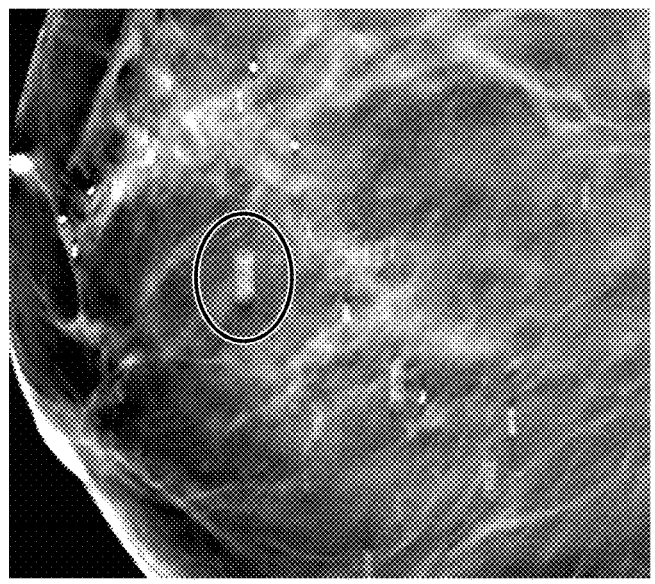
FIGS. 5A and 5B illustrate an example of an artefact that can be reduced with the proposed method according to an embodiment of the present invention (FIG. 5A) and the result obtained with this method (FIG. 5B).

A two-dimensional image 2D obtained from images of reconstructed slices using a prior art method is illustrated in FIG. 5A.

It can be seen that this image, FIG. 5A, has a sizeable artefact (encircled region in this Figure).

Figure 5B:
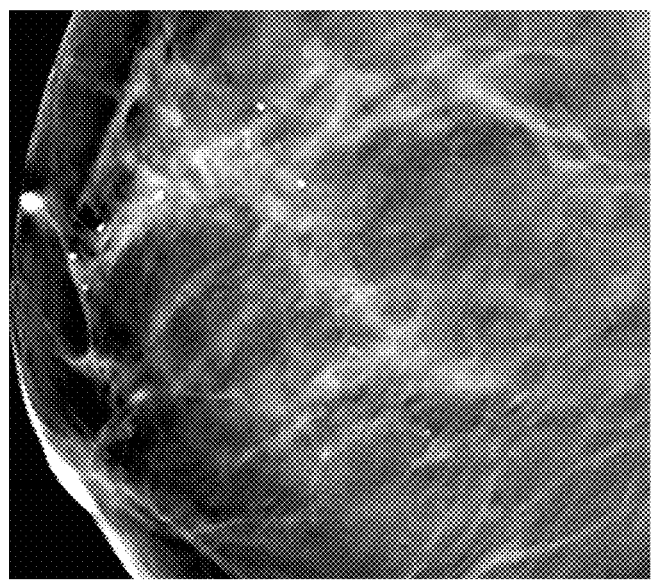

FIG. 5B illustrates the same image but obtained using the method which has just been described. As can be seen in this Figure, the artefact has been reduced therein and even eliminated.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural element with insubstantial differences from the literal languages of the claims.

What is claimed is:

1. A method for obtaining tomosynthesis images of an object of interest using an imaging system, wherein the imaging system comprises an X-ray source with an X-ray tube facing a detector on which the object of interest is positioned, the method comprising:

acquiring a plurality of projected 2D images of the object of interest in a plurality of orientations at which the X-ray source emits an X-ray beam, where the orientations are identified relative to the X-ray beam axis direction perpendicular to the detector, wherein a zero orientation is closest to the perpendicular;

applying at least one filter to the acquired projected 2D images to obtain filtered, projection images of the object of interest, wherein at least one of the at least one filter applied to the acquired projected 2D images enhances high frequencies relative to low frequencies of the correspondingly obtained filtered projection images, wherein at least one of the at least one filter applied comprises an amplification factor which varies according to x, y coordinates of pixels in the plane of the acquired projected 2D images, and wherein at least one of the at least one filter is applied in the direction corresponding to an X-ray beam scanning direction in the acquired projected 2D images;

wherein at least one of the at least one filter applied to the acquired projected 2D images is a sum of a low-pass filter and an amplification factor of a difference between a value of a pixel at a given point and a value filtered by a low-pass filter for the pixel at the given point, and wherein the low pass filter is applied as a Gaussian distribution over values of pixels within a predetermined window neighboring the pixel at the given point; and obtaining a set of tomosynthesis images of the object of interest from a backprojection of at least two of the filtered projection images, the set of tomosynthesis images being a filtered, reconstructed volume of the object of interest, wherein at least one of the at least one filter is an adaptive type filter.

2. The method according to claim 1, wherein at least one of the at least one filter applied to the acquired projected 2D images is an unsharp masking type filter.

3. The method according to claim 2, wherein at least one of the at least one filter applied to the acquired projected 2D images is a sum of a bilateral filter and an amplification of the difference between the value of a pixel at a given point and a value filtered by this bilateral filter for this pixel.

4. The method according to claim 1, wherein at least one of the at least one filter applied to the acquired projected 2D images enhances the high frequencies with an amplification factor which is a function of the local contrast of the processed projected 2D image.

5. The method according to claim 4, wherein the local contrast in a pixel of the acquired projected 2D images is the difference between the value of this pixel and the value filtered by a low-pass filter for this pixel.

6. The method according to claim 4, wherein the local contrast in a pixel of the acquired projected 2D images is the difference between the value of this pixel and the value filtered by a bilateral filter for this pixel.

7. The method according to claim 1, wherein at least one of the at least one filter applied to the acquired projected 2D images enhances the high frequencies with an amplification factor which is a function of a distance to the edge of a breast.

8. The method according to claim 1, wherein in an application to mammography, at least one of the at least one filter applied to the acquired projected 2D images is a function of a thickness of a breast tissue relative to the perpendicular to the detector and/or of the orientation at which a given projected 2D image is acquired.

9. The method according to claim 1, wherein in an application to mammography, at least one of the at least one filter applied to the acquired projected 2D images applies enhancement processing to the pixels with an amplification factor which is function of a thickness of a breast tissue relative to the perpendicular to the detector and/or of the orientation at which a given projected 2D image is acquired.

10. The method according to claim 1, wherein in an application to mammography, the frequency on and after which the amplification is applied is a function of a thickness of a breast tissue relative to the perpendicular to the detector and/or of the orientation at which a given projected 2D image is acquired.

11. The method according to claim 1, wherein after obtaining the filtered reconstructed volume, obtaining a 2D image resembling a 2D radiological image by combining an image re-projected from the filtered reconstructed volume and the acquired 2D projected image initially acquired in a given orientation of the source.

12. The method according to claim 11, wherein the combining is a pixel-by-pixel linear combination, and the backprojection and the re-projection is performed in a single computing step.

13. The method according to claim 1, comprising combining an intermediate 2D image with the acquired 2D projected image initially acquired in an orientation in which the X-ray source emits the X-ray beam in the direction perpendicular to the plane of the detector, in a pixel by pixel linear combination, to obtain a final 2D image of the object of interest.

14. An imaging system comprising:
an X-ray detector on which an object of interest is positioned;
an X-ray emitting source comprising an X-ray tube facing the X-ray detector; and
a processing unit configured to obtain a set of tomosynthesis images of the object of interest, wherein the processing unit is further configured to:
acquire a plurality of projected 2D images of the object of interest in a plurality of orientations at which the X-ray source emits an X-ray beam, where the orientations are identified relative to the X-ray beam axis direction perpendicular to the detector, wherein a zero orientation is closest to the perpendicular;
apply at least one filter to the acquired projected 2D images to obtain filtered, projection images of the object of interest,
wherein at least one of the at least one filter applied to the acquired projected 2D images enhances high frequencies relative to low frequencies in the correspondingly obtained filtered projection images, and
wherein at least one of the at least one filter applied comprises an amplification factor which varies according to x, y coordinates of pixels in the plane of the acquired projected 2D images, and
wherein at least one of the at least one filter is applied in the direction corresponding to an X-ray beam scanning direction in the acquired projected 2D images;
wherein at least one of the at least one filter applied to the acquired projected 2D images is a sum of a low-pass filter and an amplification factor of a difference between a value of a pixel at a given point and a value filtered by a low-pass filter for the pixel at the given point, and wherein the low pass filter is applied as a Gaussian distribution over values of pixels within a predetermined window neighboring the pixel at the given point; and
wherein the set of tomosynthesis images of the object of interest are obtained by performing a backprojection of at least two of the filtered projection images, the set of tomosynthesis images being a filtered reconstructed volume of the object of interest, wherein at least one of the at least one filter is an adaptive type filter.

* * * * *